United States Patent
Haddada et al.

(10) Patent No.: US 6,210,963 B1
(45) Date of Patent: Apr. 3, 2001

(54) RECOMBINANT CELLS FROM THE MONOCYTE-MACROPHAGE CELL LINE FOR GENE THERAPY

(75) Inventors: Hedi Haddada, Alfortville; Manuel Lopez, Champigny sur Marne; Michel Perricaudet, Ecrosnes, all of (FR)

(73) Assignees: Institut National de la Sante et de la Recherche Medicale, Paris (FR); Rhone-Poulenc Rorer S.A., Antony (FR)

(*) Notice: Subject to any disclaimer, the term of this patent is extended or adjusted under 35 U.S.C. 154(b) by 0 days.

(21) Appl. No.: 08/601,006

(22) PCT Filed: Aug. 22, 1994

(86) PCT No.: PCT/FR94/01019

§ 371 Date: Apr. 24, 1996

§ 102(e) Date: Apr. 24, 1996

(87) PCT Pub. No.: WO95/06120

PCT Pub. Date: Mar. 2, 1995

(30) Foreign Application Priority Data

Aug. 25, 1993 (FR) .................................................. 93 10222

(51) Int. Cl.[7] .................................................. C12N 15/00
(52) U.S. Cl. ...................... 435/325; 435/69.1; 435/320.1; 435/455; 424/93.21
(58) Field of Search ....................... 424/93.21; 435/240.2, 435/235.1, 93.21, 172.3, 323, 455, 69.1; 514/44; 935/57.62, 71

(56) References Cited

U.S. PATENT DOCUMENTS

| | | | |
|---|---|---|---|
| 5,246,921 | * | 9/1993 | Reddy et al. ........................ 514/44 |
| 5,436,151 | * | 7/1995 | McGlave et al. .................... 435/325 |
| 5,543,328 | * | 8/1996 | McClelland et al. ............. 435/320.1 |
| 5,733,548 | * | 3/1998 | Restifo et al. ..................... 424/184.1 |
| 5,756,086 | * | 5/1998 | McClelland et al. ............... 424/93.2 |

FOREIGN PATENT DOCUMENTS

0405972A1 * 1/1991 (EP) .
WO 89/05349 * 6/1989 (WO) .
93/1219 11/1992 (WO) .

OTHER PUBLICATIONS

Berkner, Current Topics in Microbiology, vol. 158: 39–61, 1992.*
La Gal La Salle et al., Science, vol. 259, pp. 988–990, Feb. 1993.*
Kohn, Current Opinion in Pediatrics, 7:56–63, 1995.*
Mulé, P.A.A.C.R., vol. 34, Mar. 1993, p. 581.*
Marshall (Aug. 1995) Science: 1050–1055.*
Mastrangelo et al. (1996) Seminar in Oncology, vol. 23, No. 1:4–21.*
Weir et al. (1993) Medical Sciences, vol. 90:9140–9144.*
Marshall (Dec. 1995) Science:1751.*
Orkin and Motulsky (Dec. 1995) NIH Report on Gene Therapy.*
Ronald Crystal (1995) Science, vol. 270, pp. 404–409.*
Coghlan (Nov. 1995) New Scientist:24–25.*
Haddada et al. (Sep. 1993) Bioc. Biphys. Res. Comm., vol. 1995, No. 3:1174–1183.*
Chu et al. (1992) Virology, vol. 188:793–800.*
Fiers et al. (Mar. 1993) Proc. Amer. Ass. Canc. Res., p. 581.*
Andreesen et al. (1990) Cancer Res. 50:7450–7456.*
Berman et al. (1989) J. of Virology, p. 3489–3498.*
Lopez et al. (1993) J. of Immun. Methods, vol. 159:29–38.*
Stefan Karlsson (1985) Proc. Natl. Acad. Sci. USA, vol. 82:158–162.*
Karp et al. (1992) J. of Immunology, vol. 149, No. 6:2076–2081.*

* cited by examiner

Primary Examiner—Scott D. Priebe
Assistant Examiner—Dave Trong Nguyen
(74) Attorney, Agent, or Firm—Finnegan, Henderson, Farabow, Garrett & Dunner, L.L.P.

(57) ABSTRACT

Cell compositions containing mononuclear phagocyte systems cells, and their use in cell therapy, e.g. adoptive immunotherapy, are disclosed.

15 Claims, 3 Drawing Sheets

RECOMBINANT CELLS FROM THE MONOCYTE-MACROPHAGE CELL LINE FOR GENE THERAPY

This application claims priority under 35 U.S.C. § 119 to French patent application number 93/10222, filed Aug. 25, 1993.

The present invention relates to cell compositions, to their preparation, to pharmaceutical compositions containing them and to their use in therapy. More especially, it relates to the isolation, culture and activation of cells of the mononuclear phagocytic system, and to their use in cell therapy, for example in adoptive immunotherapy.

The cells of the mononuclear phagocytic system comprise peripheral blood monocytes, their bone marrow or blood precursors and tissue macrophages. Monocytes are formed in the bone marrow, which they leave after maturation, passing from the peripheral blood to the tissues. Human monocytes circulating in the blood have a half-life of approximately 3 days. When it reaches the tissues, the monocyte is called a macrophage. The total number of tissue macrophages greatly exceeds the number of circulating monocytes, by a factor of approximately 400. Macrophages are found everywhere in the body, but are especially numerous in the liver (Kupffer cells), in the lymph nodes, in the lungs, in the peritoneum and in the skin (Langerhans' cells). The exact half-life of tissue macrophages is not known, but appears to be counted in months rather than in days. Lastly, the passage of monocytes from the general circulation to the tissues is irreversible.

Monocytes and macrophages are known to have numerous and important functions, including induction of immune responses in acute phases (Anonymous, Lancet ii (1985) 536–537), regulation of haematopoiesis (Sieff C. A. J. Clin. Invest. 79 (1987) 1549–1557), activation of the immune system (Unanue E. R. Annu. Rev. Immunol. 2 (1984) 395–428) and of coagulation (Prydz H., Allison A. C. Thromb. Haemost. 39 (1978) 582–591), destruction of organisms and of tumour cells (Sharma S. D., Remington J. S. Lymphokines 3 (1981) 181–212 and Carswell E. A. et al. Proc. Natl. Acad. Sci. USA 72 (1975) 3666–3670) and tissue repair and cicatrization (Korn J. H. et al., J. Clin. Invest. 65 (1980) 543–54).

Throughout the following text, a monocyte-macrophage line is defined as a line of the mononuclear system comprising peripheral blood monocytes, their bone marrow or blood precursors and tissue macrophages. It also comprises the monocytes obtained by culturing precursor cells as well as the macrophages obtained after culturing monocytic cells, under the conditions detailed in the examples (see also Andressen R. et al., Cancer Res. 50:7450; Bartholeyns J et al., Anticancer Res. 11 (1991) 1201–1204; Lopez M. et al., Journal of Immunological Methods 159 (1993) 29–38). The precursors of monocytes-macrophages comprise, in particular, pluripotent stem cells, myeloid stem cells (CFU-GEMM), myelomonocytic stem cells (CFU-GM), CFU-M, monoblasts and promonocytes.

At the present time, monocytes-macrophages are used in adoptive immunotherapy for the treatment of some types of cancer in man. These cells are purified from the circulating blood of patients, cultured ex vivo and activated with interferon γ to induce their differentiation and increase their tumoricidal power, then reinjected into the patients. However, this treatment is rather arduous for the patient, since the monocytes-macrophages have to be withdrawn regularly and frequently, the ex vivo activation requires the expenditure of considerable periods of time and interferon γ is still very expensive. For this reason, it is important to have treatments at one's disposal which are more effective, less demanding for the patient and less expensive. The present invention provides an advantageous approach to this problem. The Applicant has, in effect, shown that it is possible, using suitable vectors, to transfer genes ex vivo into monocyte-macrophage cells, thereby enabling them to be endowed with superior properties both of cytotoxicity and of stimulation of the immune system.

A first subject of the invention hence lies in a cell composition comprising cells of the monocyte-macrophage line containing a recombinant nucleic acid comprising one or more therapeutic genes under the control of regulatory elements permitting its expression.

The present invention thus makes it possible to obtain simply and effectively healthy and active monocytes-macrophages which are usable in adoptive immunotherapy for the treatment of certain pathologies, such as cancers. The present invention also makes it possible to endow monocytes-macrophages with novel or enhanced therapeutic properties compared to those of the body's monocytes-macrophages, in particular in the field of defence against infectious agents and against tumour cells or in activation of the immune system. Such cells are advantageously usable for the curative or preventive treatment of infectious (in particular viral) diseases, autoimmune diseases and immune deficiencies, or alternatively for the purpose of vaccination.

For the purposes of the invention, the term therapeutic gene denotes any gene whose transcription and, where appropriate, translation in the cell generates a product having a therapeutic effect. Such genes can comprise, in particular, those for all or part of a therapeutic protein (interleukin, interferon, tumour necrosis factor, colony stimulating factors, and the like), or for an antigenic peptide for production of a vaccine or stimulation of the immune system, or can alternatively comprise an antisense RNA capable of regulating the expression of a specific protein such as, for example, a protein of viral origin, or alternatively of interfering with the infection and/or replication cycle of a virus.

Advantageously, the gene codes for all or part of a protein capable of endowing the cells of the said line with novel or enhanced anti-infectious, anticancer or immunostimulatory properties.

More preferably, the gene is chosen from the genes coding for interferons (preferably gamma), tumour necrosis factors (preferably alpha), interleukins (IL-1 to -12) and colony stimulating factors (G-CSF, M-CSF, GM-CSF, and the like), the MDR (multi-drug resistance) gene and a gene coding for an antigen of an infectious particle or specific to a tumour (for example a surface protein of a virus, namely gp160 protein of the HIV virus in particular, or Muc-1 antigen characteristic of epithelial tumours).

In a particular mode, the subject of the present invention is cell compositions as defined above, in which the recombinant nucleic acid is carried by a vector, preferably a viral vector. The use of a vector according to the invention makes it possible, in particular, to improve the administration of the nucleic acid in the cells, and also to increase its stability in the said cells, thereby enabling a lasting effect to be obtained. Furthermore, it is possible to introduce several genes into the same vector, thereby also increasing the efficacy of the treatment.

The vector used is preferably of viral origin and, in particular, it may be chosen from adenoviruses, adeno-associated viruses (AAV), herpesvirus, vaccinia virus, cytomegalovirus (CMV), and the like.

Advantageously, the virus used is a defective virus. The term "defective virus" denotes a virus incapable of replicating in the target cell. Generally, the genome of the defective viruses used in the context of the present invention hence lacks at least the sequences needed for replication of the said virus in the infected cell. These regions may be either removed (wholly or partially), or rendered non-functional, or replaced by other sequences, and in particular by the recombinant nucleic acid. Preferably, the defective virus nevertheless retains the sequences of its genome which are needed for encapsidation of the viral particle.

An especially advantageous vector for the preparation of the cell compositions according to the invention is an adenoviral vector. The Applicant showed, in effect, that adenoviruses were capable of very effectively infecting cells of the monocyte-macrophage line, of being maintained stably therein and of expressing a therapeutic gene, which can be for an intracellular product, a membrane product or a secreted product.

Different serotypes of adenovirus exist, the structure and properties of which vary somewhat but which are not pathogenic for man, and in particular non-immunosuppressed subjects. Moreover, these viruses do not integrate in the genome of the cells they infect, and can incorporate large fragments of exogenous DNA. Among the different serotypes, it is preferable in the context of the present invention to use adenoviruses type 2 or 5 (Ad 2 or Ad 5). In the case of Ad 5 adenoviruses, the sequences needed for replication are the E1A and E1B regions.

The defective recombinant viruses used in the context of the present invention may be prepared by homologous recombination between a defective virus and a plasmid carrying, inter alia, the nucleic acid sequence as defined above (Levrero et al., Gene 101 (1991) 195; Graham, EMBO J. 3(12) (1984) 2917). Homologous recombination takes place after cotransfection of the said viruses and said plasmid into a suitable cell line. The cell line used should preferably (i) be transformable by the said elements, and (ii) contain the sequences capable of complementing the portion of the genome of the defective virus, preferably in integrated form in order to avoid the risks of recombination. As an example of a line which is usable for the preparation of defective recombinant adenoviruses, there may be mentioned the human embryonic kidney line 293 (Graham et al., J. Gen. Virol. 36 (1977) 59) which contains, in particular, integrated in its genome, the left-hand portion of the genome of an Ad5 adenovirus (12%).

Thereafter, the viruses which have multiplied are recovered and purified according to standard techniques of molecular biology.

Techniques of construction of vectors derived from adenoviruses, HSV, CMV or AAV, incorporating heterologous nucleic acid sequences, have been described in the literature and can be used in the context of the present invention [Akli et al., Nature Genetics 3 (1993) 224; Stratford-Perricaudet et al., Human Gene Therapy 1 (1990) 241; EP 185 573, Levrero et al., Gene 101 (1991) 195; Le Gal la Salle et al., Science 259 (1993) 988; Roemer and Friedmann, Eur. J. Biochem. 208 (1992) 211; Dobson et al., Neuron 5 (1990) 353; Chiocca et al., New Biol. 2 (1990) 739; Miyanohara et al., New Biol. 4 (1992) 238; WO91/18088, WO90/09441, WO88/10311].

Infection of cells of the monocyte-macrophage line may be carried out according to different protocols, at a multiplicity of infection which can be adjusted in accordance with the vector used, the gene in question, and the like, as described in the examples below.

Non-viral vectors, either chemical, of the liposome or polyamide type, or physical, such as a syringe or electroporation, may also be used.

A particular embodiment of the invention lies in a cell composition comprising precursor cells of monocytes-macrophages containing a defective recombinant adenovirus comprising one or more therapeutic genes under the control of regulatory elements permitting its expression. More especially, the precursor cells are chosen from the stem and progenitor cells of the haematopoietic system, and comprise, in particular, pluripotent stem cells, myeloid stem cells (CFU-GEMM), myelomonocytic stem cells (CFU-GM), CFU-M, monoblasts and promonocytes.

As stated above, the therapeutic gene is placed under the control of regulatory elements permitting its expression. These regulatory elements generally consist of transcription promoter sequences. These can be sequences which are naturally responsible for expression of the therapeutic gene in question, when these sequences are capable of functioning in monocytes-macrophages. They can also be sequences of different origin (responsible for the expression of other proteins, or even synthetic genes). In particular, they can be promoter sequences of eukaryotic or viral genes. For example, they can be promoter sequences originating from the genome of the cell which it is desired to infect. Similarly, they can be promoter sequences originating from the genome of a virus, including the adenovirus used as vector. In this connection, the promoters of the E1A, MLP, CMV, RSV, and the like, genes may be mentioned for example. In addition, these expression sequences may be modified by the addition of activator, regulatory, and the like, sequences. Thus, in some cases (for example, when the therapeutic gene is that for INF-$\gamma$ or TNF$\alpha$), it is especially advantageous to use, as regulatory elements, constitutive promoters permitting a continuous and high expression of the therapeutic gene. In other cases, it may be more advantageous to use a regulated promoter whose activity may be controlled. Moreover, when the inserted gene does not contain expression sequences, it may be inserted into the genome of the defective virus downstream of such a sequence.

The cell compositions according to the invention generally comprise a cell population enriched in monocytes, macrophages or their precursors. The cells can thus be monocytes, macrophages, their precursors or a mixture of these different cell types. Preferably, the compositions according to the invention possess more than 80% of monocytes, macrophages or their precursors, and still more preferably more than 90%.

The monocytes-macrophages transformed ex vivo according to the invention, especially by the use of a recombinant adenoviral vector, are hence seen to be a tool of choice for the preparation of a pharmaceutical composition, in particular an antitumour or anti-infectious composition or one intended for strengthening a patient's haematopoietic system, in particular his or her immune system.

The subject of the present invention is also a pharmaceutical composition containing as active principle cells of the monocyte-macrophage line described above.

The pharmaceutical compositions according to the invention may be administered systemically, by intratumoral injection, and the like, in accordance with the applications desired. Moreover, they may be used alone or combined with other pharmaceutical compositions.

In the foregoing, the term "combined" does not imply that the monocytes-macrophages and the other medicinal products are necessarily administered mixed or simultaneously. It also extends to any use or presentation involving their administration at time intervals which are not zero but are sufficiently short to permit an addition or a synergy in the effects produced.

In a particular embodiment, the present invention covers a pharmaceutical composition comprising cells of the monocyte-macrophage line containing a recombinant nucleic acid coding for all or part of a protein endowing the macrophage with the property of eliminating all or part of tumour cells from a body.

As stated above, mononuclear phagocytes or monocytes need to be differentiated into macrophages and then activated, essentially with interferon gamma (INF-γ), in order to become activated macrophages displaying cytotoxicity with respect to tumour cells. Hitherto, maturation of the monocyte to macrophage and activation with interferon gamma were carried out in vitro, starting with monocytic cells taken from human cytaphereses and then reinjected after activation. However, the experimental trials did not give satisfactory results, on account of problems of efficacy of activation and the large number of injections needed (at least one injection weekly, and hence one cytapheresis weekly), which proves very arduous for the patient.

The present invention makes it possible to generate ex vivo, from circulating monocytes-macrophages or their precursors, cell populations enriched in antitumour macrophages by transformation with a recombinant DNA expressing, for example, INF-γ.

A preferred mode of the present invention hence lies in a pharmaceutical composition comprising as active principle monocyte-macrophage cells as defined above containing a defective recombinant adenovirus carrying the interferon γ gene. Such cells possess, in effect, enhanced anticancer properties in adoptive immunotherapy, as a result of a constant and perpetual stimulation of the macrophages by interferon γ. The invention thus makes it possible to prepare homogeneous populations of tumorocidal human macrophages MAK (macrophages activated killers).

Among the advantages of this composition according to the invention relative to the previous treatments, its reproducibility, the low cost of the treatment and the comfort afforded to the patient by avoiding the need for regular cytaphereses may be mentioned.

Moreover, among the mediators of the antitumour activity of macrophages, TNFα (tumour necrosis factor) also plays a decisive part (Feinman et al., J. Immunol. 138 (1987) 635–640). The TNFα (or cachectin) is a cytokine essentially released from macrophages in response to a tissue destruction, a bacterial endotoxin or a viral infection, or to other cytokines (Quantin B. et al, Human Gene Transfer 219 (1991) 271–272). It is also possible, in the context of the present invention, to prepare macrophages ex vivo containing a recombinant gene expressing such a mediator, in order to generate very active cell population.

Another preferred mode of the present invention hence lies in a pharmaceutical composition comprising as active principle monocyte-macrophage cells as defined above containing a defective recombinant adenovirus carrying a gene coding for TNFα. Still more preferably, the cells of the invention contain a gene coding for a membrane form of TNFα. This membrane expression of TNFα endows the transformed cells with enhanced anticancer properties when they are used in adoptive immunotherapy. This embodiment makes it possible, in addition, to avoid a release of TNF into the extracellular medium, such a release being liable to give rise to extremely detrimental inflammatory type effects.

Advantageously, the recombinant nucleic acid codes for a TNFα from which the amino acids of the N-terminal region have been deleted, said deletion covering at least 3 amino acids and at most 20 amino acids, and preferably covering the 12 N-terminal amino acids.

In another embodiment, the present invention covers a pharmaceutical composition comprising cells of the monocyte-macrophage line containing a recombinant nucleic acid coding for all or part of a protein endowing the macrophage with the property of preventing or treating the manifestations of an infection by an infectious agent such as a virus, a retrovirus, a parasite or a bacterium, by induction or regulation of the immune response.

This use turns to good account the property of macrophages of presenting antigens at their surface, which antigen presentation stimulates the immune response of the immunocompetent cells, in particular B lymphocytes and T lymphocytes. The antigens present in the body are, in effect, taken up by the macrophages, which process them and then express them at their surface, in combination with molecules of the histocompatibility complex class II. The present invention makes it possible to develop advantageously this property of macrophages, for a general or specific stimulation of the immune system.

For general stimulation of the immune system, the therapeutic gene can be a recombinant gene expressing a compound capable of stimulating the production of MHC class II molecules, enabling cells according to the invention having enhanced antigen presentation properties to be generated; and/or a recombinant gene expressing a viral or bacterial surface antigen, enabling cells according to the invention inducing a strengthened immune defence against this type of infection to be generated. As an example of such antigens, the rabies virus glycoprotein may be mentioned in particular.

For a specific stimulation of the immune system, macrophages may be used for the presentation of defined antigens, for the purpose of vaccination.

The recombinant nucleic acid is preferably carried by an adenoviral vector which is defective in the terms defined above.

The subject of the present invention is also a method of preparation of monocytes-macrophages as are defined above, comprising the following steps:

1. withdrawal and isolation of monocytes-macrophages or their precursors from blood or bone marrow,
2. culturing of these cells,
3. transformation of these cells with a recombinant nucleic acid as defined above, and, where appropriate,
4. packaging and/or storage of the cells thereby obtained.

Withdrawal and isolation of monocyte-macrophage cells or their precursors may be performed by any technique known to a person skilled in the art. These different techniques can involve physical separation steps (centrifugation, cell sorting (FACS), and the like), and selection with immunological compounds (specific antibodies for cell markers: U.S. Pat. No. 4,965,204; EP 17,381, EP 30,450, and the like) or biochemical compounds (membrane receptor ligands: EP 405,972), and the like.

As regards monocytes-macrophages, these may be obtained from blood by different techniques, and in particular by cytapheresis (Lopez et al., J. Immunol. Methods. 159 (1992) 29) or by the use of antibodies directed against specific markers of monocyte-macrophage cells, such as CD14, CD64 or Max1. They may also be obtained ex vivo from precursor cells, by culturing under suitable conditions permitting their differentiation.

As regards the precursor cells, these may also be isolated by means of antibodies that recognize specific markers, such as: stem cells: CD33, CD34; CFU-GM and CFU-M cells: CD13, CD14, CD15, CD33, HLA DR; Monoblasts and promonocytes: CD13, CD14, CD15, CD33. Techniques which are usable in the context of the present invention are known to a person skilled in the art: see, for example, Applications EP451 611 and WO93/02182.

The cells thereby obtained may then be cultured under any sterile condition permitting their preservation, their proliferation and/or their differentiation (in the case of precursor cells). Culturing may then be performed simply in order to maintain the cells during transformation. It is, in effect, possible to transform the cells at the stage of precursor or of monocytes, which are then differentiated and/or activated in vivo after their readministration to the patient. Similarly, the differentiation/activation may be performed ex vivo, after transformation. Culturing may also be performed, in order to permit a cell proliferation and/or a cell differentiation, before performing the transformation on the mature cells (monocytes, macrophages, MAK). In particular, the proliferation of the precursors and their differentiation into monocytic cells may be performed ex vivo in the presence of growth and differentiation factors such as GM-CSF, M-CSF, interleukins IL-3, IL-4, IL-6 and IL-11, or alternatively SCF.

Culturing of isolated cells may be performed in different media known to a person skilled in the art (for example RPMI, IMDM), supplemented, inter alia, with serum and amino acids. Culturing is carried out under sterile conditions, preferably at 37° C., as illustrated in the examples. It may be performed in culture plates, or preferably in teflon bags.

The culture conditions may be adjusted by a person skilled in the art in accordance with the cell population isolated, the use desired, and the like.

Similarly, transformation of the cells with recombinant nucleic acid is performed in a sterile medium, under conditions adjusted by a person skilled in the art in accordance with the nucleic acid, the cell population isolated, and the like.

When the nucleic acid is carried by a viral vector such as an adenovirus, infection of the cells of the monocyte-macrophage line may be carried out according to different protocols, at a multiplicity of infection which can be adjusted in accordance with the vector used and the gene in question, as described in the examples below. Preferably, the monocytes-macrophages are incubated in the presence of 50 to 250 pfu per cell of purified virus, and more preferably 80 to 100 pfu/cell. Depending on the transformation conditions, the percentage of cells modified by insertion of the recombinant nucleic acid can vary from 30 to 95%.

The modified cells thereby obtained may then be packaged for the purpose of immediate use, and/or stored for the purpose of subsequent use.

For an immediate readministration, the cells are generally suspended in a phosphate buffer or in physiological saline at a concentration varying from $10^5$ to $10^9$ cells per dose.

For their storage, the cells may be frozen, preferably in the presence of preservatives such as glycerol, DMSO, and the like.

The invention thus makes it possible to carry out a treatment method comprising the administration of cells as are defined above. The cells can be those originating from the patient (autologous) or from a donor (allogeneic).

The administration may be performed in different ways. Preferably, the cells are administered by injection, preferably intravenous or intratumoral. In addition, systemic injection may be carried out by perfusion.

A particular treatment method according to the invention comprises:
1. withdrawal and isolation of monocytes-macrophages or their precursors from blood or bone marrow,
2. culturing of these cells,
3. transformation of these cells with a recombinant nucleic acid as defined above, where appropriate,
4. packaging and/or storage of the cells thereby obtained, and then
5. their administration to the patient.

The treatment of the present invention affords many advantages relative to other treatments in adoptive immunotherapy with LAK, TIL or NK (natural killers), such as, for example, the absence of toxic mediators released by the cells, the absence of proliferation of activated macrophages, the fact that the ratio of effector to target cells for the cytotoxicity is lower than in other treatments, and the fact that it does not necessitate the simultaneous injection of cytokine such as IL-2, the side effects of which are deleterious. Furthermore, it makes it possible to infect only a defined and controlled cell population, it enables the multiplicity of infection (number of viral particles per cell) to be chosen, it enables the tissues to be reached irreversibly from the blood circulation, and it makes it possible to turn to good account the central role of the macrophages in the body, both by their antitumour or anti-infectious activity and in their activity of stimulation or regulation of the immune system, as explained above. In addition, and taking account of the considerable length of life of macrophages, a handicapping repetition of treatments for the patient could be avoided.

The present invention hence affords new possibilities of more effective treatment which are less demanding for the patient, less expensive and more reproducible.

Further details of the invention will be presented in the description which follows of the possibilities of transformation of cells of the monocyte-macrophage line, and of expression of the therapeutic gene, both in cells in culture and in cells reinjected in vivo into tumours.

The examples given are not limiting but are an illustration of the feasibility of the method and of the preservation of the efficacy of the gene and of the protein expressed by the gene transferred into the macrophage, both in vitro and ex vivo and in vivo.

BRIEF DESCRIPTION OF THE DRAWINGS

FIG. 1d: uninfected control cells.

Figure 1A:
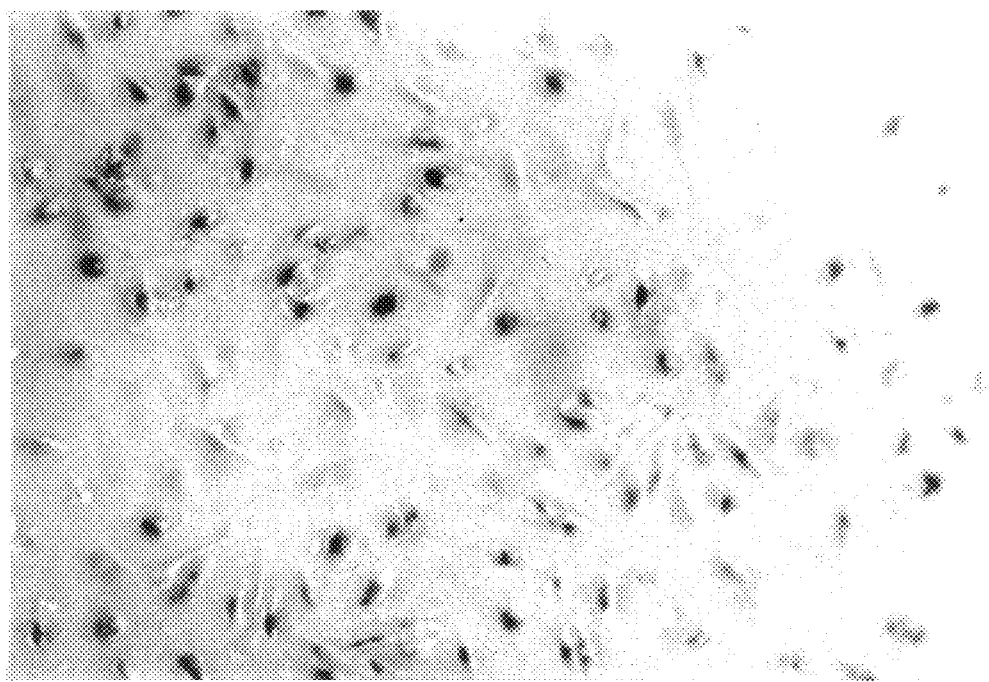
FIGS. 1a–1d. These figures show sections of macrophages derived from monocytes infected with a defective recombinant adenovirus carrying the LacZ gene of E. coli (Ad RSV β gal), 48 hours after infection (FIG. 1a), 4 days after infection (FIG. 1b) and 16 days after infection (FIG. 1c).
Figure 1B:
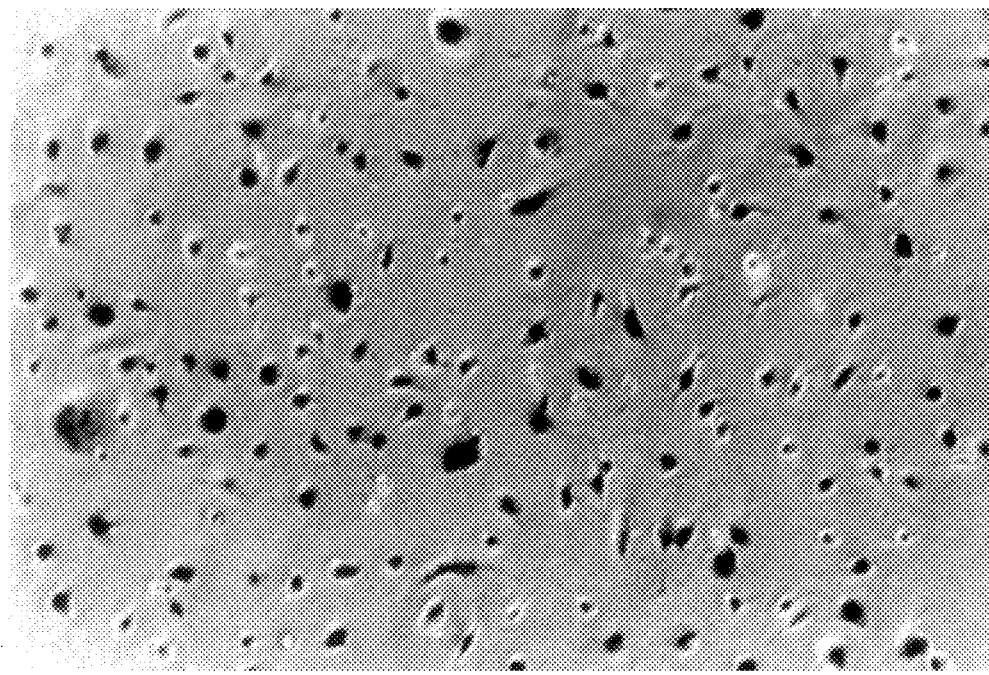
Figure 1C:
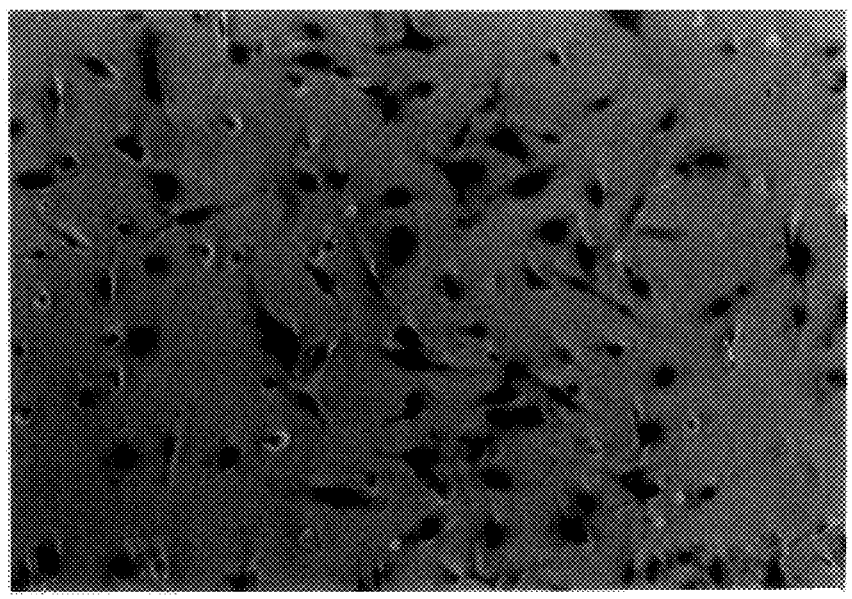
Figure 1D:
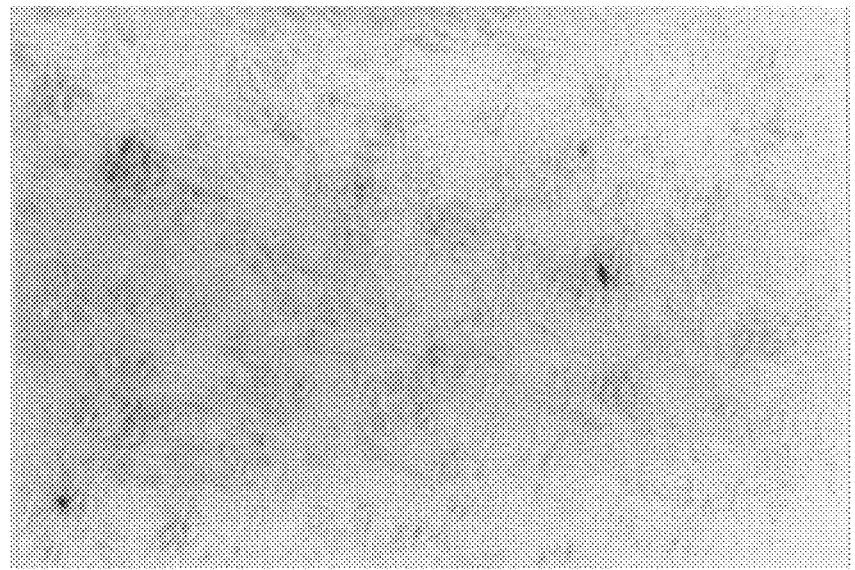

The mice display tumours induced by the subcutaneous infection of human mesothelioma tumour cells, and are treated by intratumoral injection of human monocytes-macrophages infected with Ad RVS β gal. Three days after the treatment, the tumours are extracted and fixed and the presence of β-galactosidase activity is visualized.

General Techniques of Molecular Biology

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, phenol or phenol-chloroform extraction of proteins, ethanol or isopropanol precipitation of DNA in a saline medium, transformation in *Escherichia coli,* and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Plasmids of the pBR322 and pUC type and phages of the M13 series are of commercial origin (Bethesda Research Laboratories).

For ligation, the DNA fragments may be separated according to their size by agarose or acrylamide gel electrophoresis, extracted with phenol or with a phenol-chloroform mixture, precipitated with ethanol and then incubated in the presence of phage T4 DNA ligase (Biolabs) according to the supplier's recommendations.

Filling in of 5' protruding ends may be performed with the Klenow fragment of *E. coli* DNA polymerase I (Biolabs) according to the supplier's specifications. Destruction of 3' protruding ends is performed in the presence of phage T4 DNA polymerase (Biolabs) used according to the manufacturer's recommendations. Destruction of 5' protruding ends is performed by a controlled treatment with S1 nuclease.

Mutagenesis directed in vitro by synthetic oligodeoxynucleotides may be performed according to the method according to Taylor et al. [Nucleic Acids Res. 13 (1985) 8749–8764] using the kit distributed by Amersham.

Enzymatic amplification of DNA fragments by the so-called PCR [polymerase-catalysed chain reaction, Saiki R. K. et al., Science 230 (1985) 1350–1354; Mullis K. B. and Faloona F. A., Meth. Enzym. 155 (1987) 335–350] technique may be performed using a "DNA thermal cycler" (Perkin Elmer Cetus) according to the manufacturer's specifications.

Verification of the nucleotide sequences may be performed by the method developed by Sanger et al. [Proc. Natl. Acad. Sci. USA, 74 (1977) 5463–5467] using the kit distributed by Amersham.

For the production of adenoviruses, the human embryonic kidney line 293 was used (Graham et al., J. Gen. Virol. 36 (1977) 59). This line contains, in articular, integrated in its genome, the left-hand portion of the genome of human adenovirus Ad5 (12%).

EXAMPLES

Example 1

Preparation of monocytes and macrophages

The technique of preparation of macrophages used has already been described in the literature (Lopez et al., 1993, cited above). Briefly, mononuclear cells (MNC) were separated from erythrocytes and granulocytes on a Ficoll-Hypaque (d=1.077) gradient using a Cobe 2991 blood processor, and then washed three times with phosphate buffer. A portion of the MNC was used to prepare monocytes by elutriation under the conditions given below. The other portion of the MNC was cultured ($5 \times 10^6$ per ml) in IMDM medium (Gibco, France) containing $3 \times 10^{-5}$ M 2-mercaptoethanol, 1% of non-essential amino acids, 2 mM L-glutamine, 2 mM sodium pyruvate, 100 IU per ml of penicillin, 100 μg per ml of streptomycin and 2% of AB serum, in 600 ml teflon bags, and then incubated at 37° C. in a humid atmosphere containing 5% of $CO2$ for 7 days.

The cells were then recovered, and the monocytes-macrophages purified to the extent of 95% by elutriation, using a Beckman J6ME centrifuge equipped with a J5.0 rotor and a 40 ml elutriation chamber.

Example 2

Infection of monocytes and macrophages with an adenoviral vector expressing the β-galactosidase gene (Ad. RSV βgal)

2.1. Preparation of the vector: The adenoviral vector used in this example is the vector Ad.RSV.βgal. This vector lacks the sequences needed for its replication, but nevertheless contains the sequences required for entering the cells which can be infected by it, as well as all the essential sequences needed for encapsidation of this adenovirus. It also carries the β-galactosidase gene of *E. coli* under the control of the RSV promoter. Construction of the defective recombinant adenovirus Ad.RSVβgal has been described in the literature (Stratford-Perricaudet et al., J. Clin. Invest. 90 (1992) 626). Briefly, the adenovirus Ad.RSVβGal is a defective recombinant adenovirus (from which the E1 and E3 regions have been deleted) obtained by in vivo homologous recombination between the mutant adenovirus Ad-d1324 (Thimmappaya et al., Cell 31 (1982) 543) and plasmid pAd.RSVβGal (Akli et al. 1993).

Plasmid pAd.RSVβGal contains, in the 5'→3' orientation,
  the PvuII fragment corresponding to the left-hand end of adenovirus Ad5 comprising: the ITR sequence, the origin of replication, the encapsidation signals and the E1A enhancer;
  the gene coding for β-galactosidase under the control of the RSV promoter (from Rous sarcoma virus),
  a second fragment of the adenovirus Ad5 genome which permits homologous recombination between plasmid pAd.RSVβGal and the d1324 adenovirus.

After linearization with the enzyme ClaI, plasmid pAd.RSVβGal and the d1324 adenovirus are cotransfected into line 293 in the presence of calcium phosphate to permit homologous recombination. The recombinant adenoviruses thus generated are selected by purification on plates. After isolation, the recombinant adenovirus DNA is amplified in the cell line 293, leading to a culture supernatant containing the unpurified recombinant defective adenovirus having a titre of approximately $10^{10}$ pfu/ml.

The viral particles are generally purified by centrifugation on a caesium chloride gradient according to known techniques (see, in particular, Graham et al., Virology 52 (1973) 456).

This adenovirus was used to demonstrate the possibility of transforming monocytes-macrophages and to show the efficacy of the gene transfer into these cells.

2.2. Infection of monocytes and macrophages: Macrophages or fresh monocytes were incubated overnight in the presence of 80 to 100 pfu (plaque forming unit) per cell of purified virus (Ad. RSV βgal) in complete RPMI medium ($1 \times 10^6$ cells per ml). The cells were washed to remove free viral particles and then reincubated in fresh complete RPMI medium in teflon bags or in 12-well culture plates. At different times, aliquots of cells were washed, fixed and tested for the presence of β-galactosidase activity.

β-Galactosidase activity was tested for in cells after infection with the recombinant adenovirus using histochemical methods as described in (Stratford-Perricaudet et al., (Hum. Gene Ther. 1 (1990) 241). Briefly, cells are incubated in the presence of X-gal to disclose β-gal activity, which is then visualized by the appearance of a blue coloration in the nucleus of cells containing the β-gal gene and counterstained with haematoxylin and eosin.

Example 3

Demonstration of gene transfer into human monocytes or macrophages derived from human monocytes transformed with the recombinant adenoviral vector carrying the β-galactosidase gene.

3.1. Expression of β-galactosidase activity in monocytes-macrophages in cell culture The efficacy of gene transfer with the adenoviral vectors was tested in purified monocytes and in macrophages derived from these same monocytic cells. Mononuclear blood cells obtained by cytapheresis were separated on a Ficoll gradient as described in Example 1. A portion of the MNC suspension was subjected to elutriation, and the monocytes thereby obtained were used in the infection tests (Example 2). A second portion of the MNC suspension was cultured for 6 to 7 days, permitting the differentiation of monocytes into macrophages as described in Example 1. After this period of culture, the macrophages were also purified by elutriation. The macrophages thus purified are twice as large as the monocytes, and express the Max 1 antigen specific to differentiation at their surface. The expression of CD 14 of HLA-DR and of CD 64 is also increased significantly when comparison is made with the starting monocytes. A portion of the macrophages obtained from the monocytes in culture was then activated by adding 250 IU/ml of recombinant interferon gamma approximately 18 hours before the end of culturing, according to the protocol described in Lopez et al. (J. Immunotherapy 11 (1992) 209–217). This activation enables activated macrophages capable of being active in anti-infectious immunotherapy to be obtained.

The purified monocytes or purified macrophages, either after 6 days of culture (that is to say before activation with interferon gamma) or after 7 days of culture (after activation with interferon gamma), were infected with 80 to 100 pfu (plaque-forming units) per cell of the recombinant adenovirus Ad. RSV βgal.

After infection overnight, the medium is removed and the cells are washed and reincubated in fresh complete medium, either in teflon bags or in twelve-well plates. The cells were then fixed and tested for β-galactosidase activity at different time intervals after infection. Expression of β-galactosidase in the cell nucleus indicates the efficacy of gene transfer and of gene expression.

The results obtained are presented in FIG. 1. They show the detection of β-galactosidase activity at different times after infection of macrophages derived from monocytes treated with interferon. Similar results are obtained with cells not activated with interferon gamma. Depending on the preparation, 40 to 80% of the macrophages express β-galactosidase activity in their nucleus between 2 and 4 days after infection. The expression of β-galactosidase continues up to 3 weeks after infection (FIG. 1C). It is understood that, by increasing the multiplicity of infection, the percentage of cells expressing the recombinant gene may be increased. It is thus possible to obtain cell compositions in which 95% or more of the cells are transformed.

3.2. Expression of β-galactosidase after intratumoral injection of monocytes-macrophages infected with the recombinant adenovirus in nude mice With a view to testing whether infected monocytes-macrophages can express an exogenous gene in tumours in vivo, monocytes-macrophages infected with the recombinant adenovirus were injected into tumours induced in nude mice.

Nude mice were first subjected to a subcutaneous injection of $2\times10^6$ human mesothelioma tumour cells (HIB cells). The tumours (approximately 4 mm in diameter) induced by this injection were then treated by intratumoral injection of human monocytes-macrophages infected with Ad.RSVβgal, obtained in Example 3.1. For injection, the infected human monocytes-macrophages were suspended in phosphate buffer. The doses injected were $2\times10^6$ cells per mouse. Three days after the treatment, the tumours were extracted and fixed and the presence of β-galactosidase activity is visualized.

Figure 2:
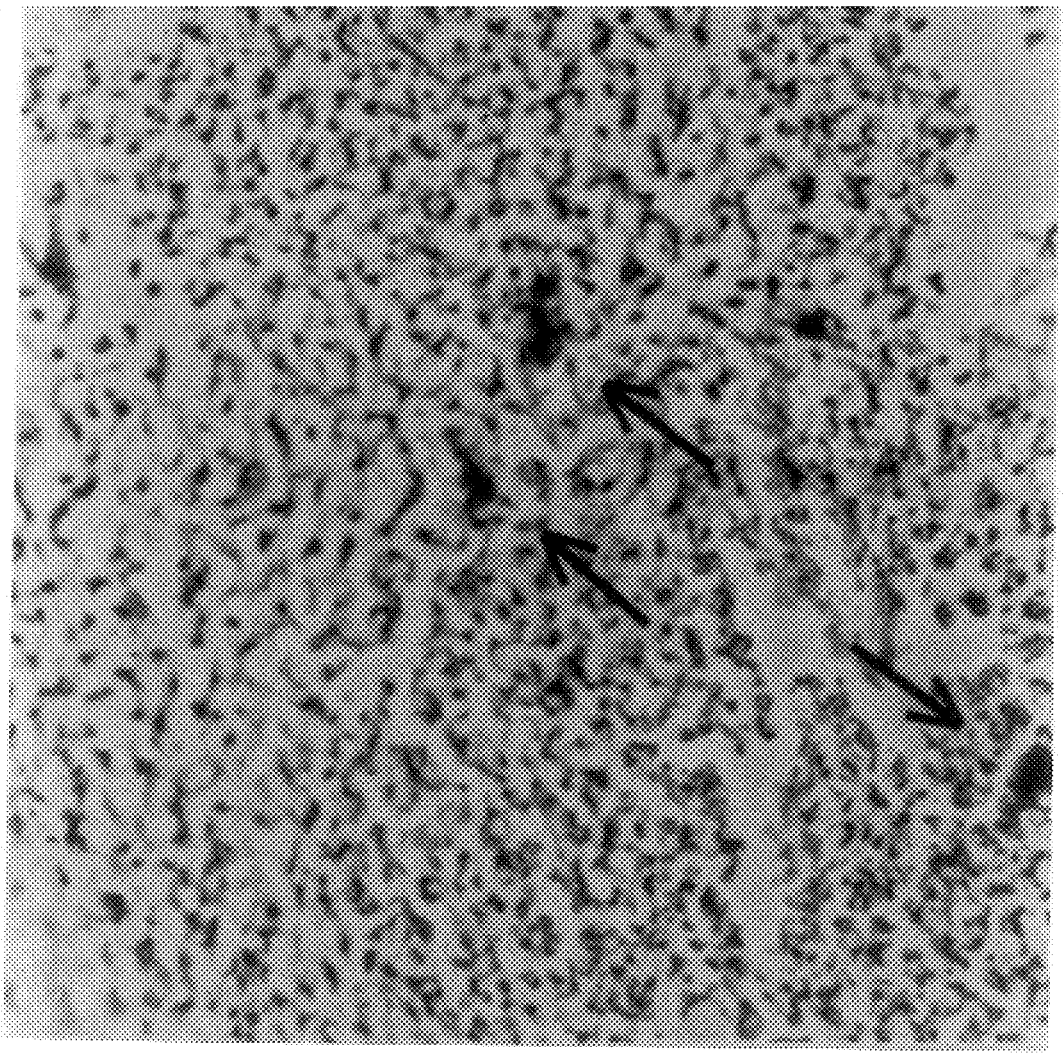
FIG. 2. Detection of β-galactosidase activity expressed in monocytes-macrophages transformed with adenovirus Ad RSV β gal, after intratumoral injection into nude mice.

The results obtained are presented in FIG. 2. They show clearly that β-galactosidase activity is found in the tumour 3 days after the treatment, and that the monocytes-macrophages administered are hence capable of substantially colonizing the tumour and of expressing a recombinant gene therein.

Example 4

Transfer of a mutated TNFα gene into macrophages derived from human blood monocytes TNFα or cachectin is a cytokine released essentially from macrophages in response to a tissue destruction, a bacterial endotoxin and a viral ailment, and to other cytokines. TNF is produced in the form of a prohormone of 233 amino acids (26 kDa). The mature protein contains 157 amino acids (17 kDa) and results from the removal of an N-terminal sequence of 76 amino acids. Activated monocytes-macrophages synthesize membrane TNFα, and have a cytotoxic action on their target by cell—cell contact (effect of membrane TNFα of 26 kDa), as well as by local release of soluble TNFα (17 kDa). This is different from what takes place during septic shock, which shock is considered to result partially from an acute or chronic activation of monocytes, leading to release of the secreted form of TNF (Perez et al., Cell 63 (1990) 251). Since the time when TNFα was cloned and expressed in *E. coli* (Pennica et al. 1984), large amounts have been available for clinical trials. However, the therapeutic use of TNFα in man is limited by its considerable toxicity and the side effects it produces (cachexia, fever, headaches, fatigue, hypertension). In colorectal cancer, a recent clinical trial has shown that considerable toxicity is seen at doses which are insufficient for obtaining antitumour activity (Kemeny et al., 1990).

The present invention enables the antitumour power of macrophages to be increased without generating toxicity associated with soluble TNFα. The present invention makes it possible, in effect, to generate macrophages transfected by the membrane form of TNFα. Moreover, the macrophages of the invention thereby obtained display another great advantage: in effect, whereas soluble (secreted) TNFα has a short plasma half-life of approximately 20 minutes, the macrophages of the invention can remain at the periphery of the tumour for several days, affording the hope of a longer-lasting antitumour activity resulting from contact between the macrophage carrying TNF and the tumour cell.

Macrophages thus activated were obtained by infection of macrophages derived from monocytes or of monocytes with recombinant adenoviruses as are described in Example 2, but in which the therapeutic gene is that for a mutated TNFα.

More specifically, the mutated gene was obtained in the following manner. The membrane form of TNFα possesses two cleavage sites, one located between amino acids −1 and +1 (position +1 represents the beginning of the mature protein), the other located in the +13 region (Perez et al., 1990, cited above). The deletion of amino acids 1 to 12 prevents cleavage in the 26 kDa form while maintaining the cytotoxicity at the cell—cell contact zones. Mutuations of human TNFα were carried out by directed mutagenesis; they correspond to the mutants Δ+1, Δ1–12 described by C. Perez et al., 1990, cited above. The efficacy of the constructions of mutated TNF is evaluated by transient expression in eucaryotic (cos) cells, looking for the membrane, intracellular and secreted forms of TNF using anti-TNF antibodies and measuring its biological activity. A recombinant adenovirus comprising the mutated gene prepared above is then constructed; and the biological activity of the TNF synthesized is monitored: (a) with respect to line L 929, by the technique of cytolysis zones in agar, which technique discloses lysis dependent on cell—cell contact, and (b) by the inhibition of incorporation of tritiated thymidine into U 937 (histocytic cells from a human lymphoma), K 562 (cells originating from a chronic myelogenic leukaemia) and LS 174 T (colon adenocarcinoma) cells in culture, as well as with respect to blast cells taken from leukaemic patients. In vivo antitumour activity is then tested in an animal model and consists in implanting human tumours into nude mice and then in treating these mice with systemic injections of macrophages transfected with the modified TNFα gene, as described above in Example 3. The antitumour effect is evaluated relative to control mice treated with a placebo or with untransfected macrophages.

Example 5

Macrophages derived from monocytes or monocytes transformed with the recombinant adenovirus containing the interferon gamma gene and endowing the macrophages with enhanced antitumour activity The interferon gamma gene was introduced into the adenoviral vector described above, and the recombinant adenovirus was used to transform cells of monocytes or of macrophages derived from monocytes.

The macrophages obtained after differentiation in RPMI medium, as described above in Example 1, express interferon gamma constitutively, hence it is no longer necessary to treat the macrophages for 18 to 24 hours in order to obtain the requisite cytotoxic and antitumour effect. Macrophages constitutively expressing interferon gamma may thus be used in adoptive anticancer immunotherapy, either by systemic injection or by direct injection into the tumours.

What is claimed is:

1. A preparation of isolated autologous differentiated monocyte-macrophage cells selected from the group consisting of monocytes and macrophages, wherein the differentiated monocyte-macrophage cells comprise a replication defective recombinant adenovirus which comprises a heterologous gene under the control of an element regulating expression of the gene.

2. The preparation according to claim 1, wherein the gene encodes a functional protein selected from the group consisting of interferon, tumour necrosis factor, interleukin, colony stimulating factor, multi-drug resistance, an antigen of an infectious particle and a tumor specific antigen.

3. The preparation according to claim 2, wherein the colony stimulating factor is selected from the group consisting of G-CSF, M-CSF, and GM-CSF.

4. The preparation according to claim 1, wherein the gene encodes a functional interferon-γ or tumour necrosis factor-α.

5. The preparation according to claim 1, wherein the gene encodes a viral or bacterial surface antigen.

6. The preparation according to claim 1 in injectable form.

7. The preparation according to claim 1 in intravenous or intratumoral injectable form.

8. The preparation according to claim 1 in perfusion form.

9. The preparation according to claim 1, comprising $10^5$ to $10^9$ cells.

10. A preparation comprising monocyte-macrophage cells selected from the group consisting of monocytes and macrophages containing a replication defective recombinant adenovirus which comprises a gene encoding a functional interferon-γ.

11. A preparation comprising isolated autologous differentiated monocyte-macrophage cells selected from the group consisting of monocytes and macrophages, wherein the monocyte-macrophage cells comprise a replication defective recombinant adenovirus which comprises a gene encoding a functional tumour necrosis factor-α.

12. The preparation according to claim 11, wherein the tumour necrosis factor-α gene encodes a membrane form of tumour necrosis factor-α.

13. A preparation of isolated autologous differentiated monocyte-macrophage cells selected from the group consisting of monocytes and macrophages, wherein the monocyte-macrophage cells comprise a replication defective recombinant adenovirus which expresses an HIV surface antigen.

14. A method of preparing a cell preparation which comprises isolated autologous differentiated monocyte-macrophage cells selected from the group consisting of monocytes and macrophages, wherein the differentiated monocyte-macrophage cells comprise a replication defective recombinant adenovirus which comprises a heterologous gene under the control of an element regulating expression of the gene, which method comprises isolating autologous differentiated monocytes-macrophages from blood, culturing the monocytes-macrophages, and transforming the cultured monocytes-macrophages with a replication defective recombinant adenovirus which comprises a heterologous gene under the control of an element regulating expression of the gene.

15. The method of claim 14 further comprising packaging the transformed monocytes-macrophages for storage.

* * * * *